(12) United States Patent
Wadhwa

(10) Patent No.: US 12,665,054 B2
(45) Date of Patent: *Jun. 23, 2026

(54) SYSTEM AND METHOD FOR ANALYZING SPECTRAL DATA USING ARTIFICIAL INTELLIGENCE

(71) Applicant: Vionix Biosciences Inc., Belmont, CA (US)

(72) Inventor: Vivek Wadhwa, Belmont, CA (US)

(73) Assignee: Vionix Biosciences Inc., Belmont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/335,786

(22) Filed: Sep. 22, 2025

(65) Prior Publication Data

US 2026/0011412 A1 Jan. 8, 2026

Related U.S. Application Data

(63) Continuation of application No. 18/828,382, filed on Sep. 9, 2024, now Pat. No. 12,437,842.

(60) Provisional application No. 63/541,177, filed on Sep. 28, 2023.

(51) Int. Cl.
| | |
|---|---|
| *G16B 40/10* | (2019.01) |
| *G16H 10/40* | (2018.01) |
| *G16H 15/00* | (2018.01) |
| *G16H 50/70* | (2018.01) |

(52) U.S. Cl.
CPC ............. *G16B 40/10* (2019.02); *G16H 10/40* (2018.01); *G16H 15/00* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 10,209,178 B2 | 2/2019 | Carvalho Sousa et al. | |
| 10,914,683 B2 | 2/2021 | Mahadevan-Jansen et al. | |
| 11,002,681 B2 | 5/2021 | Umapathy et al. | |
| 11,079,279 B2 | 8/2021 | Pyun et al. | |
| 11,337,643 B2 | 5/2022 | Fan et al. | |
| 11,650,195 B2 | 5/2023 | Kaditz et al. | |
| 11,698,370 B2 | 7/2023 | Goldman et al. | |
| 12,055,495 B2 | 8/2024 | Guadiuso et al. | |
| 2018/0098726 A1 | 4/2018 | Pyun et al. | |
| 2021/0020276 A1 | 1/2021 | Da Costa Martins | |
| 2021/0149361 A1 | 5/2021 | Jungbauer et al. | |
| 2021/0231597 A1 | 7/2021 | Emokpae et al. | |
| 2022/0203407 A1 | 6/2022 | Kumar et al. | |
| 2022/0268751 A1 | 8/2022 | Farkas et al. | |
| 2022/0412892 A1 | 12/2022 | Xie et al. | |
| 2023/0034263 A1 | 2/2023 | Zhao et al. | |
| 2023/0222654 A1 | 7/2023 | Fan et al. | |
| 2025/0111900 A1 | 4/2025 | Wadhwa | |

FOREIGN PATENT DOCUMENTS

| | | |
|---|---|---|
| WO | 2025003926 A1 | 1/2025 |

OTHER PUBLICATIONS

Murtaza et al. Computer Science Review (2023) vol. 48:40 pages.
Outeiral et al. (WI REs Com put. Mol. Sci. (2021) vol. 11 :23 pages).
Zitnik et al. (Information Fusion (2019) vol. 50:71-91).
Arabi et al. AMB Express (2023) vol. 13, No. 61, 12 pages, doi: 10.1186/s13568-023-01569-0.
Bagcioglu et al. Front. Microbiol. (2019) vol. 10, No. 902, 10 pages, doi: 10.3389/fmicb.2019.00902.
Gaudiuso et al. Spectrochimica Acta Part B: Atomic Spectroscopy (2020) vol. 171, 15 pages, doi: 10.1016/j.sab.2020.105931.
Pokrajac et al. Applied Spectroscopy (2014) vol. 68, No. 9, 9 pages, doi: 10.1366/14-07488.
Wang et al. Analytica Chimica Acta (2021) vol. 1179, 11 pages, doi: 10.1016/j.aca.2021.338822.

*Primary Examiner* — Lori A. Clow
(74) *Attorney, Agent, or Firm* — Neo IP

(57) ABSTRACT

A system provides for an ability to automatically identify one or more chemical components of a sample, especially a biological fluid sample, based on analysis of spectral data by at least one artificial intelligence module. The artificial intelligence module is able to be trained on a plurality of spectral data samples having known concentrations of individual chemicals and elements. The system is preferably used for spectral techniques such as UV/vis and near-infrared (NIR) spectrophotometry, but is also able to be used for other forms of spectroscopic techniques, including mass spectrometry, infrared (IR) spectrometry, X-ray spectroscopy, Raman spectrometry, or nuclear magnetic resonance (NMR) spectrometry.

20 Claims, 15 Drawing Sheets
(14 of 15 Drawing Sheet(s) Filed in Color)

BIDISTILLED WATER WITH DIFFERENT
TEMPERATURE / PRESSURE & PLASMA POWER CONDITIONS

Relative intensity [arbitrary units] vs wavelength [nm].

NORMALIZED BIDISTILLED VS MBG WATER COMPARISON

Relative intensity [per unit normalized] vs wavelength [nm].

SODIUM DOUBLET DLINES AT 588.9950 AND 589.5924 [nm]
DIFFERENT PRESSURE / PLASMA POWER & CONCENTRATION CONDITIONS

Relative intensity [arbitrary units] vs wavelength [nm]
(NaCl solution Zoomed @589 nm).

Relative intensity [arbitrary units] vs wavelength [nm] (zoom into 300 ~ 400 nm).

VOLATILE ORGANICS: ACETONE & ETHANOL V/S MOLBIO GRADE WATER

DATA-ACETONE
DATA-ETHANOL
DATA-MOLBIOGRADE-WATER

Relative intensity [arbitrary units] vs wavelength [nm].

Relative intensity [arbitrary units] vs wavelength [nm] (zoom into 350 ~ 650 nm).

ACETONE AND ETHANOL DELTAS
(SUBSTRACTING MOL BIO WATER SPECTRA AS ZERO BASELINE)

Relative intensity [arbitrary units] vs wavelength [nm] (zoom into 350 ~ 650 nm).

Relative intensity [arbitrary units] vs wavelength [nm] (zoom into 350 ~ 650 nm).
Normalized @ 482 [nm] peak for pattern comparison.

Relative intensity [arbitrary units] vs wavelength [nm] (zoom into 465 ~ 500 nm).
Normalized @ 482 [nm] peak for pattern comparison.
Peak at 485 ~ 486 [nm] appears only in ethanol.

SYSTEM AND METHOD FOR ANALYZING SPECTRAL DATA USING ARTIFICIAL INTELLIGENCE

CROSS-REFERENCE TO RELATED APPLICATIONS

This application is related to and claims priority from the following US patents and patent applications: this application is a continuation of U.S. patent application Ser. No. 18/828,382, filed Sep. 9, 2024, which claims priority from and the benefit of U.S. Provisional Patent Application No. 63/541,177, filed Sep. 28, 2023. Each of the documents referenced above are incorporated herein by reference in their entirety.

BACKGROUND OF THE INVENTION

1. Field of the Invention

The present invention relates to spectroscopic analysis techniques, and more specifically to artificial intelligence-based spectroscopic analysis for multi-element and multi-macromolecule systems in biological analytes, especially medical fluid and breath samples.

2. Description of the Prior Art

It is generally known in the prior art to provide spectroscopic analysis for various substances, including medical fluids, in order to determine a chemical composition of those samples. Furthermore, it is known to provide artificial intelligence analysis techniques for analyzing results of techniques such as mass spectrometry.

Prior art patent documents include the following:

US Patent Pub. No. 2021/0231597 for Fluid property sensor and fluid particle sensor by inventors Emokpae et al., filed Jan. 22, 2021 and published Jul. 29, 2021, discloses a method, system and apparatus for sensing fluids. A fluid sensor is configured to analyze a fluid utilizing impedance spectroscopy. Capacitive impedance of fluids is sensed and measured. Inductive impedance of suspended particles in fluids is measured. An electrochemical fingerprint of the properties of the fluid or of the particles within the fluid is generated. Fluid analytics data is generated from sensor signal data of the fluids under test. Trainable artificial intelligence algorithms are used to generate fluid analytics data.

U.S. Pat. No. 11,698,370 for Home toilet system for monitoring urine components in real time while urination by inventors Goldman et al., filed Sep. 29, 2021 and issued Jul. 11, 2023, discloses a system for urine sample analysis, where the system may include one or more transmitters for transmitting radiation; one or more sensors that are configured to receive received radiation that passed through the urine sample and to generate detection signals indicative of an intensity of the received radiation at multiple frequencies; detaching elements that are configured to detach the one or more transmitters and the one or more sensors to a toilet bowl; and a processor that is configured to participate in the urine sample analysis for determining a content of the urine sample based on the detection signals.

US Patent Pub. No. 2023/0034263 for Compositions and methods for spatial profiling of biological materials using time-resolved luminescence measurements by inventors Zhao et al., filed Nov. 19, 2020 and published Feb. 2, 2023, discloses compositions, including products of manufacture and kits, and methods, for in situ spatial profiling of biological materials such as DNA, RNA and protein in cells, tissues, and organisms for investigating biology and for conducting biomarker/drug discovery and development, and for clinical pathology and diagnosis. In alternative embodiments, provided are compositions, including products of manufacture and kits, and methods, for spatially determining, visualizing or quantifying target biological materials comprising in situ staining of a biological sample with one or a plurality of probes that are labeled with light-emitting moieties that exhibit or are encoded with distinct luminescence lifetime (and, optionally, spectrum) characteristics; followed by time-resolved luminescence imaging, measurement and analysis.

US Patent Pub. No. 2022/0268751 for Apparatus and method for multimode analytical sensing of items such as food by inventors Farkas et al., filed Feb. 25, 2022 and published Aug. 25, 2022, discloses a multimode biological sample inspection apparatus and method. The apparatus includes an illumination hardware arrangement comprising transmission and sensing hardware configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample by constructing a multidimensional dataset comprising at least one spatial dimension and at least one spectral dimension from the scan results and analyzing the multidimensional dataset. The processing hardware is configured to employ the attributes of at least one biological sample and alter the protocol.

U.S. Pat. No. 10,209,178 for Optical system for parameter characterization of an element of body fluid or tissue by inventors Carvalho Sousa et al., filed Jan. 31, 2014 and issued Feb. 19, 2019, discloses a biophotonic device for the point-of-care, real-time, non-invasive determination of parameters with diagnostic relevance, in particular an optical system for parameter characterization of an element of body fluid or tissue comprising an optical device which comprises: a light source for emitting light onto the element; and a spectrometer for recording the spectrum of light from the element, said light from the element being of transmittance, reflectance or Raman scattering of the emitted light by said element; the optical system further comprising a data processing module configured to: convert the recorded spectrum by a conversion matrix into a standardized spectrum, wherein said conversion matrix has been obtained by calibrating the optical system spectrum response against a spectrum reference; pre-process the converted spectrum; correlate, for parameter quantification, the converted pre-processed spectrum with pre-obtained spectral bands for each parameter; said spectrum being contained within uv-vis-nir wavelengths. Also methods of operating said system.

U.S. Pat. No. 11,650,195 for Iterative medical testing of biological samples by inventors Kaditz et al., filed Sep. 26, 2018 and issued May 16, 2023, discloses a system performing one or more magnetic resonance (MR) measurements on at least a portion of a biological life form. Moreover, the system quantitatively simulates an MR response of at least the portion of the biological life form, and compares the one or more MR measurements and the quantitative simulation to obtain a first test result. Next, the system determines one or more additional medical tests to perform. In response, the system accesses the biological sample in storage, and performs the one or more additional medical tests on at least a second portion of the biological sample to obtain one or more additional test results. Furthermore, the system computes a second test result based at least in part on the first test result and the one or more additional test results, where the second test result has an improved accuracy relative to the first test result.

US Patent Pub. No. 2021/0149361 for Real time monitoring of product purification by inventors Jungbauer et al., filed Apr. 4, 2017 and published May 20, 2021, discloses a method and device which allows in real-time the determination of concentration, purity and potency of a biological product during purification and/or concentration processes in order to intervene into the process, either for process control or real time release. The properties of the process stream are continuously monitored by at least two online sensors and with the aid of multivariate statistical analysis so that concentration, purity and potency is determined in real time.

US Patent Pub. No. 2022/0203407 for Sorting based on chemical composition by inventors Jungbauer et al., filed Mar. 16, 2022 and published Jun. 30, 2022, discloses systems and methods for classifying and sorting materials in order to produce a collection of materials that are composed of a particular chemical composition in the aggregate. The system may utilize a vision system and one or more sensor systems, which may implement a machine learning system in order to identify or classify each of the materials. The sorting is then performed as a function of the classifications.

US Patent Pub. No. 2023/0222654 for Machine learning systems and methods for assessment, healing prediction, and treatment of wounds by inventors Fan et al., filed Mar. 2, 2023 and published Jul. 13, 2023, discloses machine learning systems and methods for prediction of wound healing, such as for diabetic foot ulcers or other wounds, and for assessment implementations such as segmentation of images into wound regions and non-wound regions. Systems for assessing or predicting wound healing can include a light detection element configured to collect light of at least a first wavelength reflected from a tissue region including a wound, and one or more processors configured to generate an image based on a signal from the light detection element having pixels depicting the tissue region, determine reflectance intensity values for at least a subset of the pixels, determine one or more quantitative features of the subset of the plurality of pixels based on the reflectance intensity values, and generate a predicted or assessed healing parameter associated with the wound over a predetermined time interval.

U.S. Pat. No. 11,337,643 for Machine learning systems and techniques for multispectral amputation site analysis by inventors Fan et al., filed Aug. 24, 2020 and issued May 24, 2022, discloses certain aspects relating to apparatuses and techniques for non-invasive and non-contact optical imaging that acquire a plurality of images corresponding to both different times and different frequencies. Additionally, alternatives described herein are used with a variety of tissue classification applications including assessing the presence and severity of tissue conditions, such as necrosis and small vessel disease, at a potential or determined amputation site.

SUMMARY OF THE INVENTION

The present invention relates to spectroscopic analysis techniques, and more specifically to artificial intelligence-based spectroscopic analysis for multi-element and multi-macromolecule systems in biological analytes, especially medical fluid and breath samples.

It is an object of this invention to provide automatic analysis of spectrographic test results to identify chemical compositions of sample fluids, especially medical fluids in order to improve speed and accuracy of results to patients.

In one embodiment, the present invention is directed to an artificial intelligence (AI)-based system for automatically identifying biological molecules in a fluid sample, including one or more servers configured to receive multi-dimensional training data from one or more spectrometers or chemical analysis devices, and an AI module on the one or more servers configured to automatically develop characteristic profiles for a plurality of molecules or sets of molecules based on the multi-dimensional training data, wherein the one or more servers receives experimental data for a medical fluid sample from a testing spectrometer, and wherein the AI module automatically generates a report with indications of present identified molecules based on comparison of the experimental data to the characteristic profiles for the plurality of molecules or sets of molecules.

In another embodiment, the present invention is directed to an artificial intelligence (AI)-based method for automatically identifying biological molecules in a fluid sample, including one or more servers receiving multi-dimensional training data from one or more spectrometers or chemical analysis devices, an AI module on the one or more servers automatically developing characteristic profiles for a plurality of molecules or sets of molecules based on the multi-dimensional training data, the one or more servers receiving experimental data for a medical fluid sample from a testing spectrometer, and the AI module automatically generating a report with indications of present identified molecules based on comparison of the experimental data to the characteristic profiles for the plurality of molecules or sets of molecules.

In yet another embodiment, the present invention is directed to an artificial intelligence (AI)-based system for automatically identifying biological molecules in a fluid sample, including one or more cloud servers configured to receive training data from one or more spectrometers or chemical analysis devices, and an AI module on the one or more cloud servers configured to automatically develop characteristic profiles for a plurality of molecules or sets of molecules based on the training data, wherein the training data received from the one or more spectrometers or chemical analysis devices is combined with public datasets and/or additional third party datasets, wherein the one or more cloud servers receives experimental data for a medical fluid sample from a testing spectrometer, and wherein the AI module automatically generates a report with indications of present identified molecules based on comparison of the experimental data to the characteristic profiles for the plurality of molecules or sets of molecules.

In another embodiment, the present invention is directed to methods to analyze functional groups of chemicals in a mixture of compounds and compositions.

These and other aspects of the present invention will become apparent to those skilled in the art after a reading of the following description of the preferred embodiment when considered with the drawings, as they support the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
FIG. 1 illustrates a chart of intensity versus wavelength for analysis of bidistilled water at different temperatures and pressures generated by the present invention.

The present invention is generally directed to spectroscopic analysis techniques, and more specifically to artificial intelligence-based spectroscopic analysis for multi-element and multi-macromolecule systems in biological analytes, especially medical fluid and breath samples.

In one embodiment, the present invention is directed to an artificial intelligence (AI)-based system for automatically identifying biological molecules in a fluid sample, including one or more servers configured to receive multi-dimensional training data from one or more spectrometers or chemical analysis devices, and an AI module on the one or more servers configured to automatically develop characteristic profiles for a plurality of molecules or sets of molecules based on the multi-dimensional training data, wherein the one or more servers receives experimental data for a medical fluid sample from a testing spectrometer, and wherein the AI module automatically generates a report with indications of present identified molecules based on comparison of the experimental data to the characteristic profiles for the plurality of molecules or sets of molecules.

In another embodiment, the present invention is directed to an artificial intelligence (AI)-based method for automatically identifying biological molecules in a fluid sample, including one or more servers receiving multi-dimensional training data from one or more spectrometers or chemical analysis devices, an AI module on the one or more servers automatically developing characteristic profiles for a plurality of molecules or sets of molecules based on the multi-dimensional training data, the one or more servers receiving experimental data for a medical fluid sample from a testing spectrometer, and the AI module automatically generating a report with indications of present identified molecules based on comparison of the experimental data to the characteristic profiles for the plurality of molecules or sets of molecules.

In yet another embodiment, the present invention is directed to an artificial intelligence (AI)-based system for automatically identifying biological molecules in a fluid sample, including one or more cloud servers configured to receive training data from one or more spectrometers or chemical analysis devices, and an AI module on the one or more cloud servers configured to automatically develop characteristic profiles for a plurality of molecules or sets of molecules based on the training data, wherein the training data received from the one or more spectrometers or chemical analysis devices is combined with public datasets and/or additional third party datasets, wherein the one or more cloud servers receives experimental data for a medical fluid sample from a testing spectrometer, and wherein the AI module automatically generates a report with indications of present identified molecules based on comparison of the experimental data to the characteristic profiles for the plurality of molecules or sets of molecules.

Spectroscopic techniques are a quintessential method of analyzing chemical composition of samples. Various spectroscopic techniques rely on different techniques to treat a sample and rely on different phenomena of molecules in order to identify the sample. For example, infrared (IR) spectroscopy involves emitting infrared radiation on a sample and then detecting the absorbance of the radiation from the molecules within at different wavelengths. The vibrational modes of particular functional groups or bond types within the material tend to absorb infrared radiation at different wavelengths, allowing for determination of at least properties of one or more chemical components within the sample. Most commonly, spectroscopic tests are performed for samples with one or only a few unknown components, allowing for simpler, albeit not always very simple, investigation of the composition of a small number of chemicals. However, difficulty arises in these techniques where there are many components having different functional groups, especially where those different components are larger and have more functional components.

Difficulties arise, in part, because samples with many types of molecules tend to produce a high density of peaks within the technique that are difficult for a human operator to accurately distinguish or determine whether higher peaks indicate multiple components with the same functional group or a single component having the group, but having high concentration. For medical fluids, these issues have partially been resolved by utilizing a wide array of tests for the same sample types, where the variety of tests are able to detect the presence or absence of specific molecules or classes of molecules. For example, for blood analysis, a wide variety of tests, from enzymatic tests and flow cytometry, to Raman spectroscopy and beyond are used to provide a more comprehensive view of the blood sample. However, the use of this wide variety of test techniques also necessitates higher expense and longer time than is ideal for informing patients about potentially serious issues that require resolution. Most commonly, not all of these tests are capable of being performed in the doctor's office or hospital, extending the time even further to account for transport of samples and communication with an external lab. Therefore, a method is needed to simplify analysis of medical fluids to utilize a single device (or a relatively low number of devices) in order to reduce time and money required for analysis.

Referring now to the drawings in general, the illustrations are for the purpose of describing one or more preferred embodiments of the invention and are not intended to limit the invention thereto.

The present invention includes a device (e.g., a computer, a smart phone, a tablet, a smart watch, etc.) including a processor and a memory operable to receive and analyze spectrographic test data from at least one spectrographic analysis device, especially a spectrophotometric analysis device. In one embodiment, the device includes at least one server in network communication directly with the at least one spectrographic analysis device, or through an intermediary device, such as a computer, tablet, smart phone, etc. In this embodiment, analysis is able to be done remotely, providing for additional computational power that is potentially not feasible using an in-house computer. In one embodiment, the at least one server includes at least one quantum processor operable to assist in performing analysis on the spectrographic test data.

The present invention is operable to produce a multi-dimensional dataset of spectral data or other chemical analysis data generated by one or more spectrometers or other chemical analysis devices. This multi-dimensional data allows the AI model of the present invention to leverage diverse and orthogonal information from each dimension in the dataset to allow for a final classification of molecules or compounds in a medical fluid sample. In one embodiment, the dataset is multimodal, meaning that the system of the present invention is capable of combining different analysis modalities (e.g., UV spectra, Raman spectra, IR spectra, mass spec, etc.) whether produced by a single device or multiple different devices. This combination of multiple modalities allows the system to become more granular and precise in its evaluations. In addition to different spectral or other analysis data, the multi-dimensional dataset is further able to take into account additional modalities, including patient demographics (e.g., race, sex, age, etc.), patient medical history, patient vitals, and/or other parameters, which often assist in providing additional context to the measurements taken of the medical fluid. In one embodiment, patient demographic data or other similar data is connected to the chemical analysis (e.g., spectroscopic data)

as metadata in order to allow for association of the patient demographics with the particular samples. The multi-dimensional dataset is able to be generated at the chemical analysis devices or at the server itself as it combines data from different data sources.

The present invention is preferably able to be used for analysis of medical fluids (i.e., fluids generated by a human body or the body of another, non-human animal). Furthermore, the term "fluid" as used herein is used to refer to both gasses and liquids. Examples of medical fluids able to be analyzed by the present invention include blood, saliva, urine, sweat, lymph, amniotic fluid, synovial fluid, mucus, semen, and/or other medical fluids. Examples of spectroscopic techniques whose results are able to be examined according to the present invention include ultraviolet-visual (UV/Vis) Spectroscopy, near infrared (NIR) spectroscopy, infrared (IR) spectroscopy, Raman spectroscopy, mass spectrometry, nuclear magnetic resonance (NMR) spectroscopy (including continuous wave, Fourier-Transform, solid state NMR, magic-angle spinning NMR, etc.), X-ray spectroscopy, optical emission spectroscopy (OES), atomic emission spectroscopy (AES), Mossbauer spectroscopy, and/or other forms of spectroscopic and spectrophotometric techniques. In one embodiment, the medical fluid sample is ionized via a non-thermal plasma source, including a strong electric field, as described in U.S. Provisional Patent Application No. 63,533,053, which is incorporated herein by reference in its entirety. However, one of ordinary skill in the art will understand that the invention of the present invention is not inherently limited to use with medical fluids and is able to be used to identify biological contaminants in other uses cases, including, but not limited to, determining the quality of water.

The processor includes at least one artificial intelligence module operable to automatically analyze the spectrographic test data and identify one or more likely chemical composition represented by the spectrographic test data. In one embodiment, the at least one artificial intelligence module produces a plurality of potential chemical compositions of the sample with associated likelihoods for each composition based on closeness of match to previous data, or a model built based on analysis of previous data. In one embodiment, the at least one artificial intelligence module is trained based on previous spectrographic test data stored in at least one database and/or in the memory of the device. Preferably, this previous spectrographic test data corresponds with samples with known chemical compositions, such that the at least one artificial intelligence module is able to correlate the output spectrographic test data with the known chemical composition to build a more accurate model. In this way, the system develops a characteristic profile for each molecule, or set of molecules such that, under similar conditions and showing similar spectra, the system is able to identify particular molecules with a particular degree of certainty. In one embodiment, the training data further includes synthetic data (i.e., data not from actual tests) in order to expedite the model learning simple spectra of common molecules. The use of an artificial intelligence module is especially important for medical fluids, which frequently have many complex molecules in them that are unlikely to show simple peaks that are easily understood or reasoned out by a researcher (due to factors such as density of peaks and greater noise).

In one embodiment, data produced by spectrometers or other chemical analysis devices associated with the present invention are able to be brought into a single cloud environment, optionally also including additional public dataset or other supporting datasets produced by third parties in order to aggregate and strengthen the power of the model of the present invention to allow for the most powerful models for spectral data ever known. In one embodiment, the report is able to include not only an identification of which molecules are present, but also an indication of the concentration of those molecules and/or a probability value associated with the identification to indicate a degree of certainty to which the model identified the reported molecule.

In one embodiment, the system is operable to produce interactive reports detailing what chemicals or molecules are present in a sample in different formats depending on the preference of the reader or consumer of the data.

In one embodiment, the at least one artificial intelligence module utilizes principal components analysis (PCA) and/or linear discriminant analysis (LDA) for feature compression in order to feed into the downstream machine learning (ML) model used by the present invention.

The system is operable to utilize a plurality of learning techniques including, but not limited to, machine learning (ML), artificial intelligence (AI), deep learning (DL), neural networks (NNs), artificial neural networks (ANNs), support vector machines (SVMs), transformers (e.g., generative pre-trained transformers), Markov decision process (MDP), random forest, multiple layer perceptron, recurrent neural networks, generalized adversarial networks, and/or natural language processing (NLP). The system is operable to use any of the aforementioned learning techniques alone or in combination.

Further, the system is operable to utilize predictive analytics techniques including, but not limited to, machine learning (ML), artificial intelligence (AI), neural networks (NNs) (e.g., long short term memory (LSTM) neural networks), transformers (e.g., generative pre-trained transformers), deep learning, historical data, and/or data mining to make future predictions and/or models. The system is preferably operable to recommend and/or perform actions based on historical data, external data sources, ML, AI, NNs, and/or other learning techniques. The system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Figure 2:
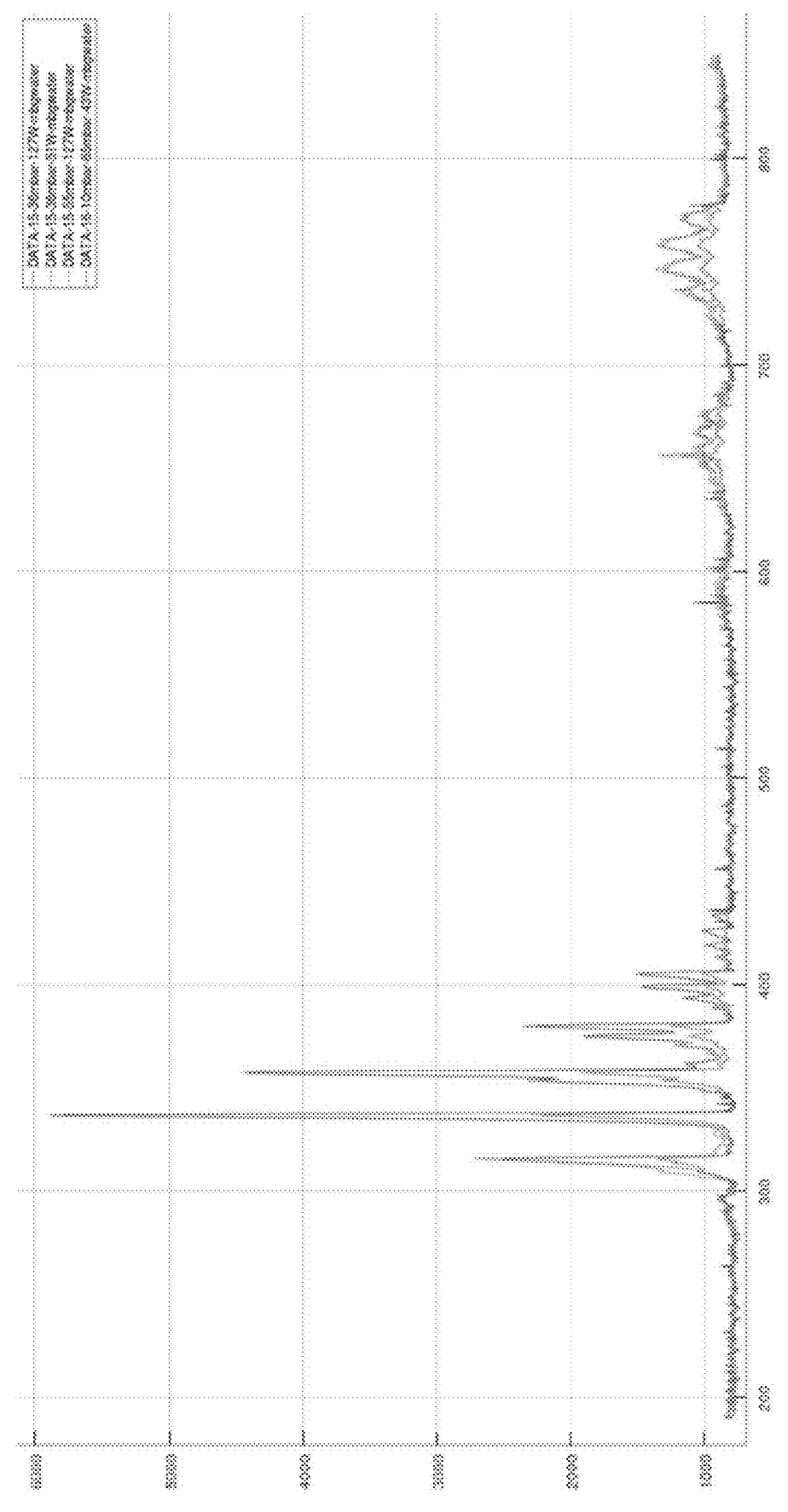
FIG. 2 illustrates a chart of intensity versus wavelength for analysis of molecular biology grade (MBG) water at different temperatures and pressures generated by the present invention.
Figure 3:
FIG. 3 illustrates a chart of intensity versus wavelength, comparing normalized peaks of bidistilled and molecular biology grade (MBG) generated by the present invention.

FIGS. 1-14 provide examples of spectral data able to be incorporated into the present invention to identify particular molecules and demonstration of the ability of such spectra to distinguish the presence and/or concentration of particular molecules based on FIG. 1 illustrates a chart of intensity versus wavelength for analysis of bidistilled water at different temperatures and pressures generated by the present invention. FIG. 2 illustrates a chart of intensity versus wavelength for analysis of molecular biology grade (MBG) water at different temperatures and pressures generated by the present invention. FIG. 3 illustrates a chart of intensity versus wavelength, comparing normalized peaks of bidistilled and molecular biology grade (MBG) generated by the present invention. As shown in FIGS. 1-3, the device disclosed in the present invention has sufficient sensitivity to detect even different peaks between differently purified or ionized levels of water, demonstrating a high capability for detection of other molecules. For the purposes of analysis, the MBG water spectra was used as a baseline for detecting other molecules as discussed further below.

Figure 4:
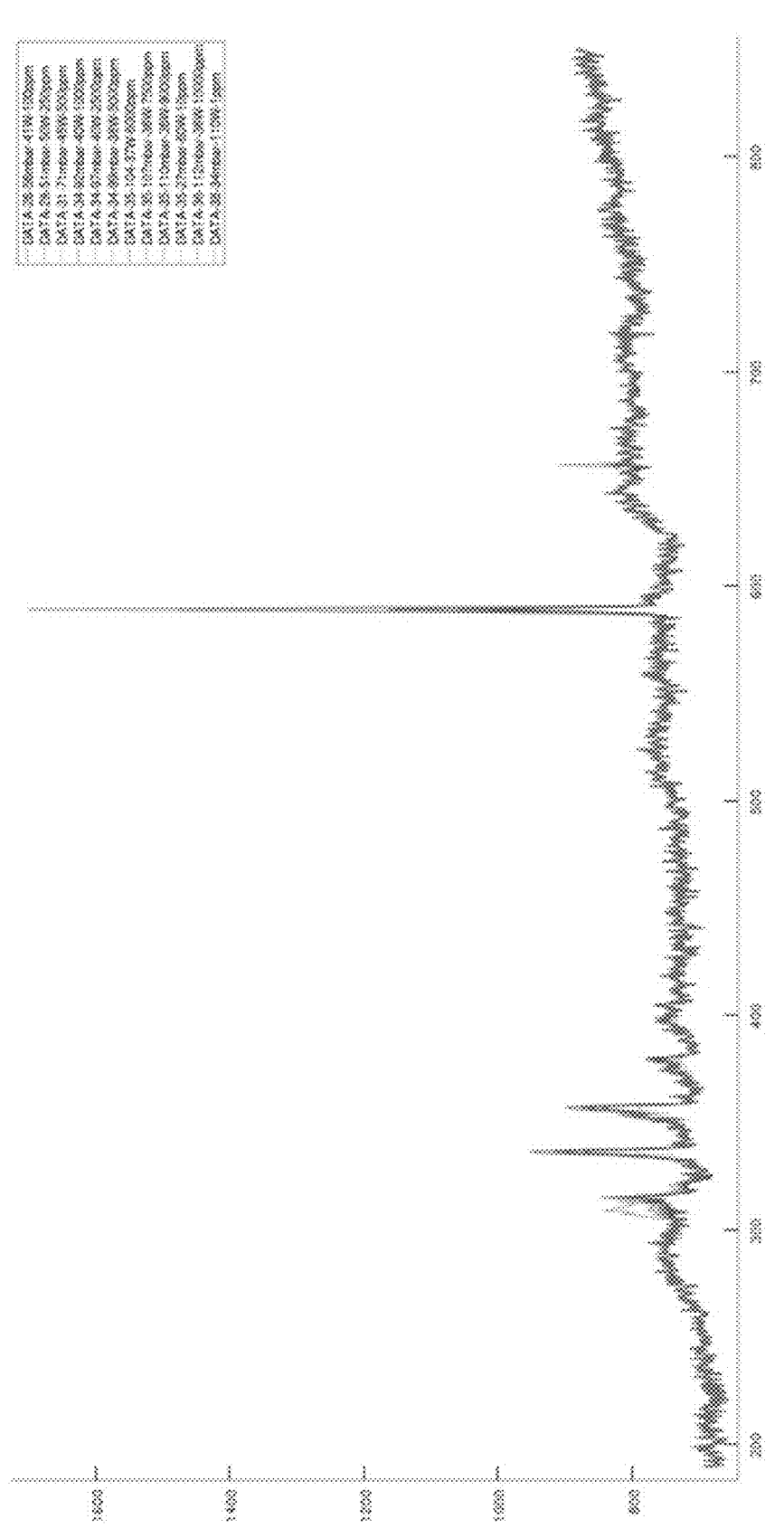
FIG. 4 illustrates a chart of intensity versus wavelength, comparing normalized peaks of sodium chloride (NaCl) at different concentrations, pressures, and plasma power conditions generated by the present invention.
Figure 5:
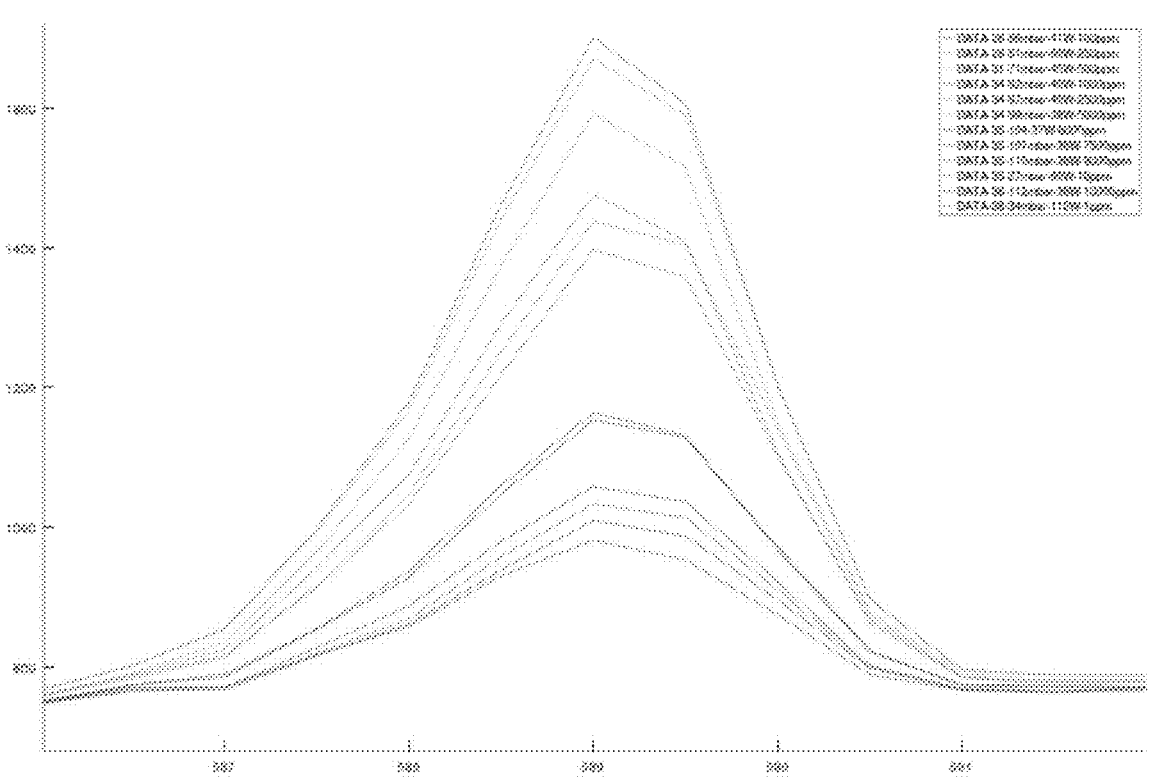
FIG. 5 illustrates a zoomed-in intensity versus wavelength chart for sodium chloride at different pressures, concentrations, and plasma power conditions, focused around a peak at 589 nm generated by the present invention.

FIG. 4 illustrates a chart of intensity versus wavelength, comparing normalized peaks of sodium chloride (NaCl) at different concentrations, pressures, and plasma power conditions generated by the present invention. FIG. 5 illustrates a zoomed-in intensity versus wavelength chart for sodium chloride at different pressures, concentrations, and plasma power conditions, focused around a peak at 589 nm generated by the present invention. By checking the peak at different conditions, including concentrations, pressures, and plasma power conditions, the system demonstrating relatively consistent peaks in the spectrum, but with the peaks having different intensities depending on those conditions. The charts in FIGS. 4-5 demonstrate that, generally, higher peaks are detecting at higher concentrations, allowing the system to have an ability to distinguish amounts of certain chemicals, in addition to identify their presences based on characteristic peaks.

Figure 6:
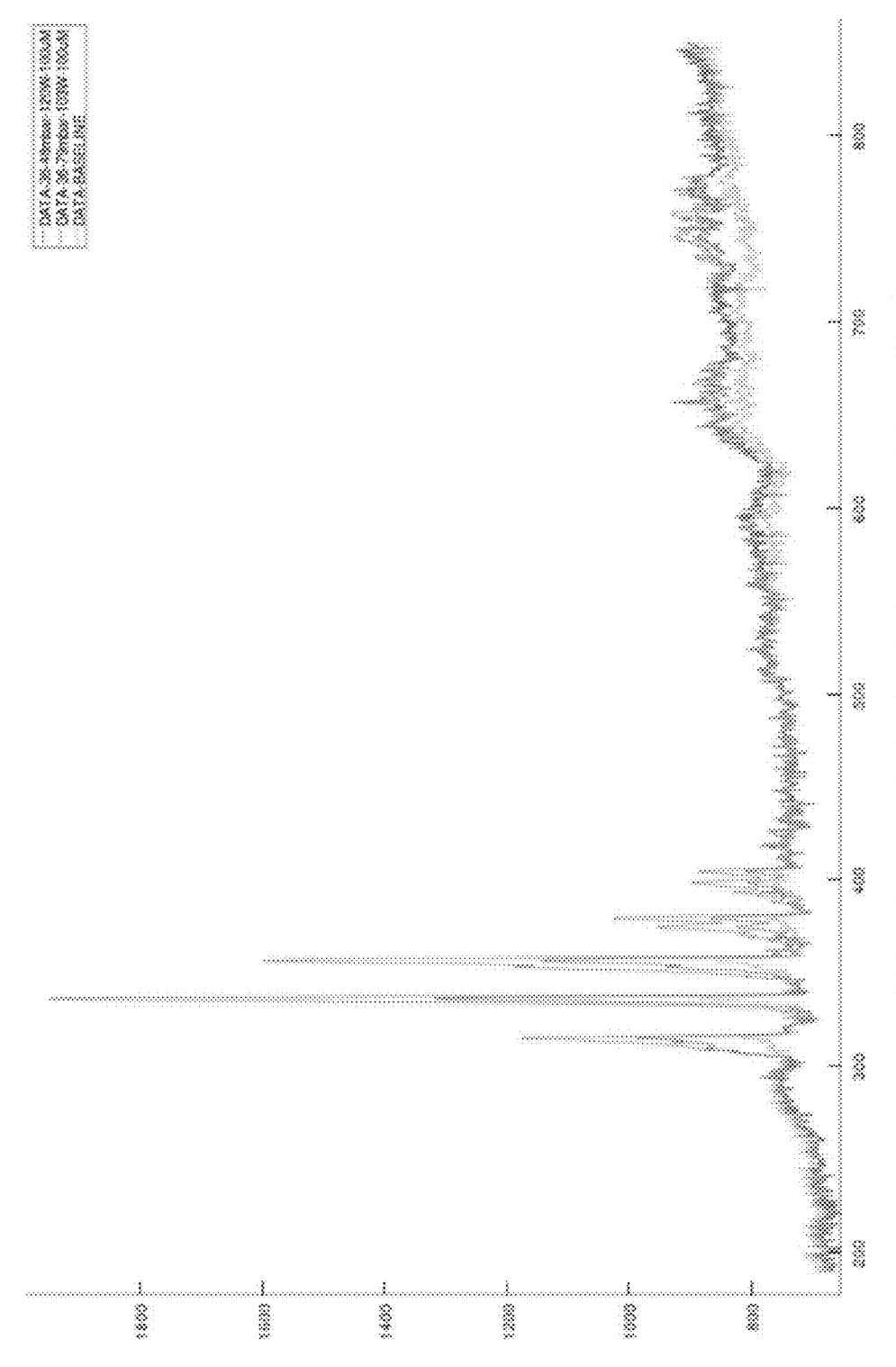
FIG. 6 illustrates a chart of intensity versus wavelength, comparing samples with dATP at different pressure, concentration, and plasma power conditions relative to a water baseline generated by the present invention.
Figure 7:
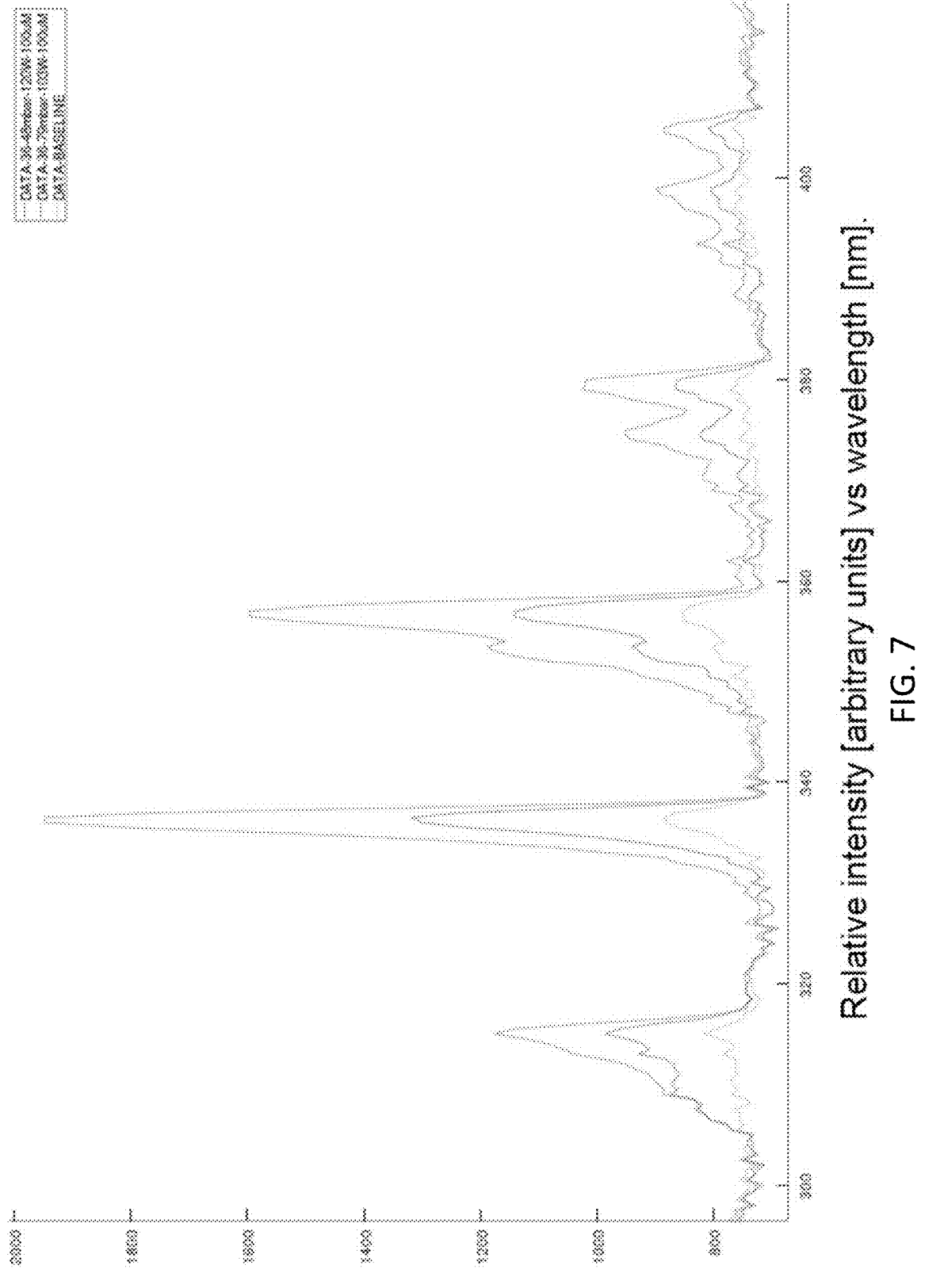
FIG. 7 illustrates a chart of intensity versus wavelength, comparing samples with dATP at different pressure, concentration, and plasma power conditions relative to a water baseline, zoomed in around 360 nm, generated by the present invention.

FIG. 6 illustrates a chart of intensity versus wavelength, comparing samples with dATP at different pressure, concentration, and plasma power conditions relative to a water baseline generated by the present invention. FIG. 7 illustrates a chart of intensity versus wavelength, comparing samples with dATP at different pressure, concentration, and plasma power conditions relative to a water baseline, zoomed in around 360 nm, generated by the present invention. FIGS. 6 and 7 show characteristic peaks that are higher than baseline peaks for the water sample, showing detection of the dATP.

Figure 8:
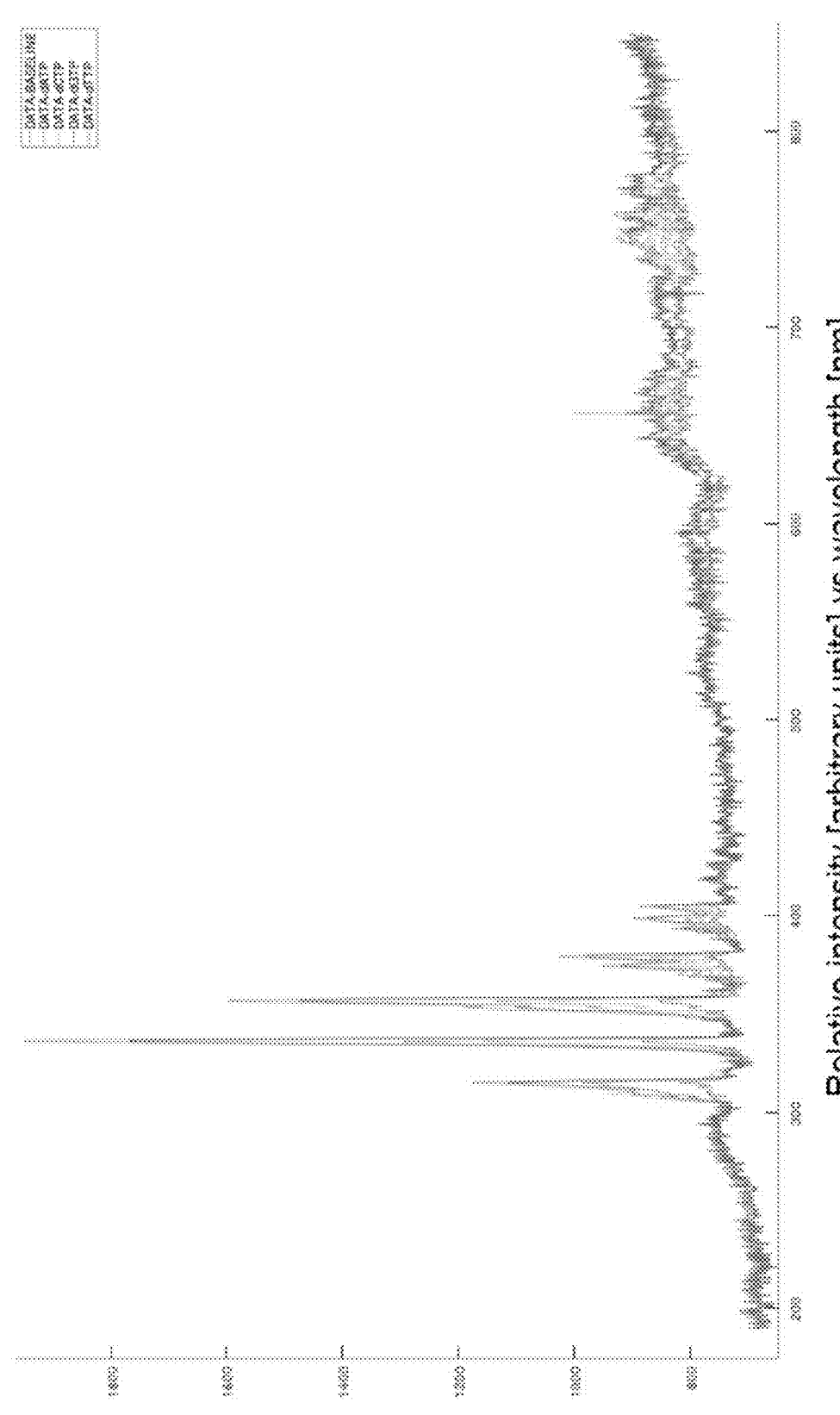
FIG. 8 illustrates a chart of intensity versus wavelength, comparing samples with dATP, dCTP, dGTP, dTTP relative to a water baseline generated by the present invention.
Figure 9:
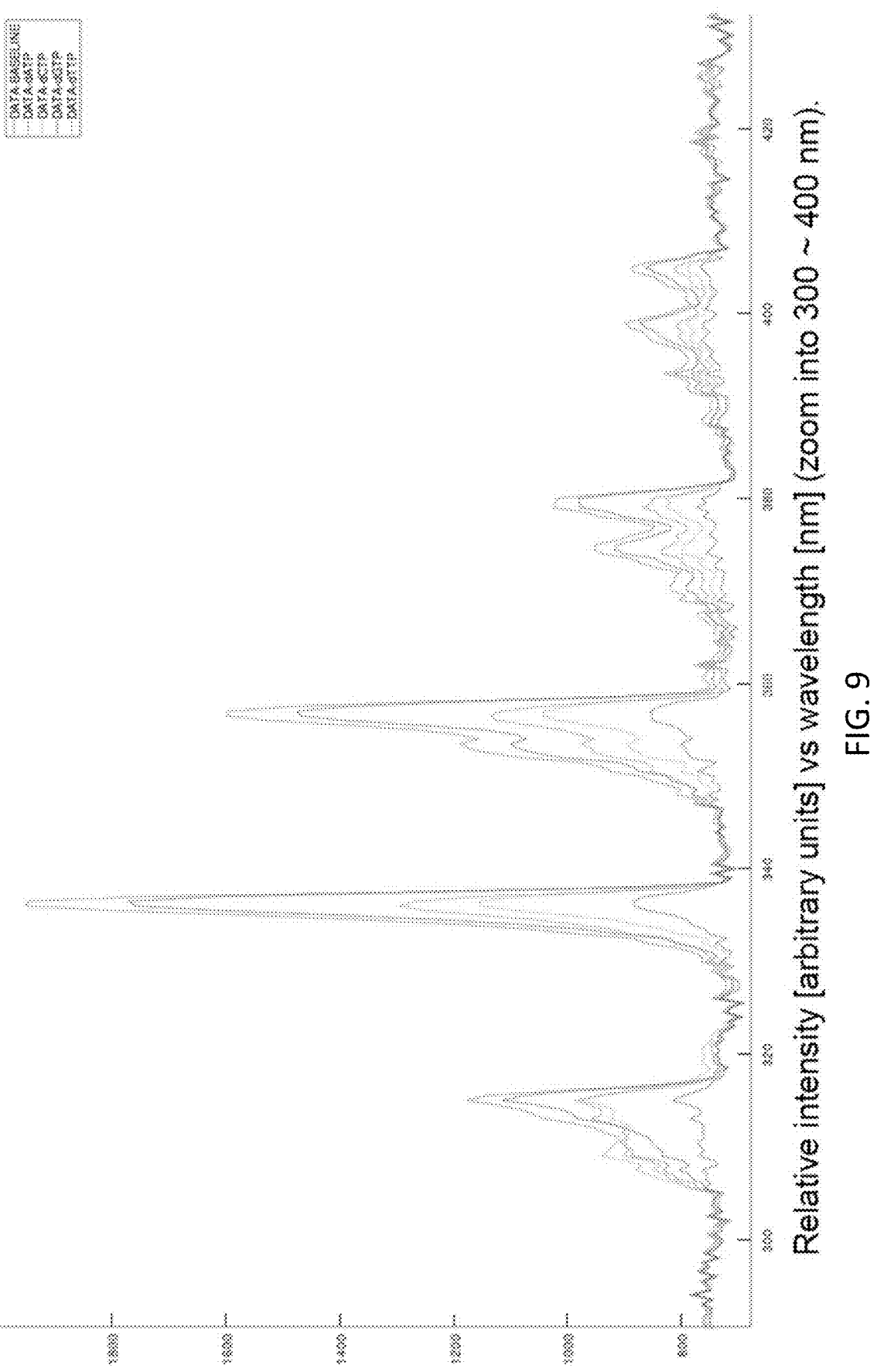
FIG. 9 illustrates a chart of intensity versus wavelength, comparing samples with dATP, dCTP, dGTP, dTTP relative to a water baseline, zoomed in between 300 and 400 nm, generated by the present invention.

FIG. 8 illustrates a chart of intensity versus wavelength, comparing samples with dATP, dCTP, dGTP, dTTP relative to a water baseline generated by the present invention. FIG. 9 illustrates a chart of intensity versus wavelength, comparing samples with dATP, dCTP, dGTP, dTTP relative to a water baseline, zoomed in between 300 and 400 nm, generated by the present invention. FIGS. 8-9 demonstrate that the system is not only capable of detecting a compound present versus a water baseline, but also differentiation between different, but similar, compounds.

Figure 10:
FIG. 10 illustrates a chart of intensity versus wavelength, comparing samples with acetone, ethanol, and MBG water generated by the present invention.
Figure 11:
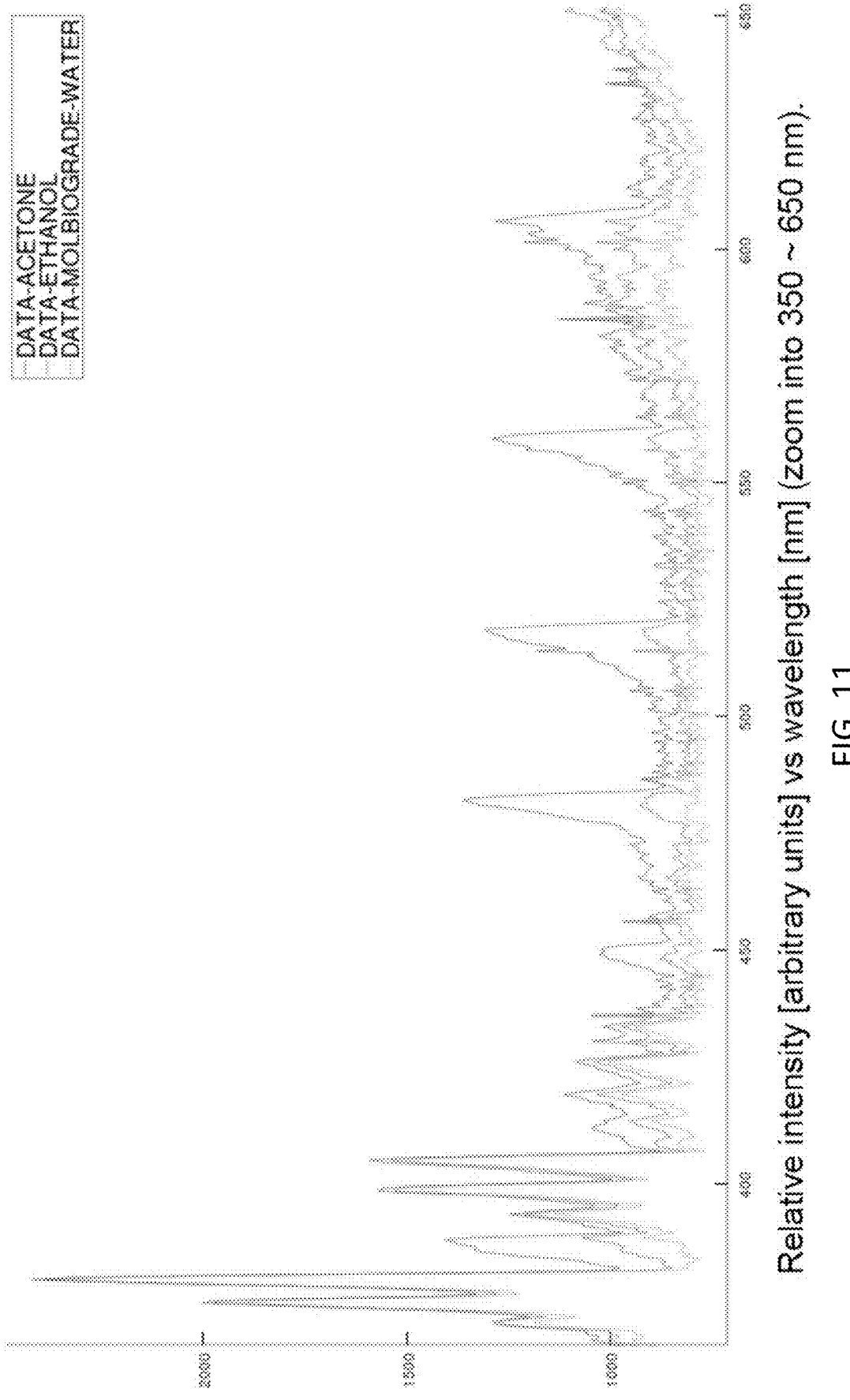
FIG. 11 illustrates a chart of intensity versus wavelength, comparing samples with acetone, ethanol, and MBG water, zoomed in between 350 and 650 nm, generated by the present invention.
Figure 12:
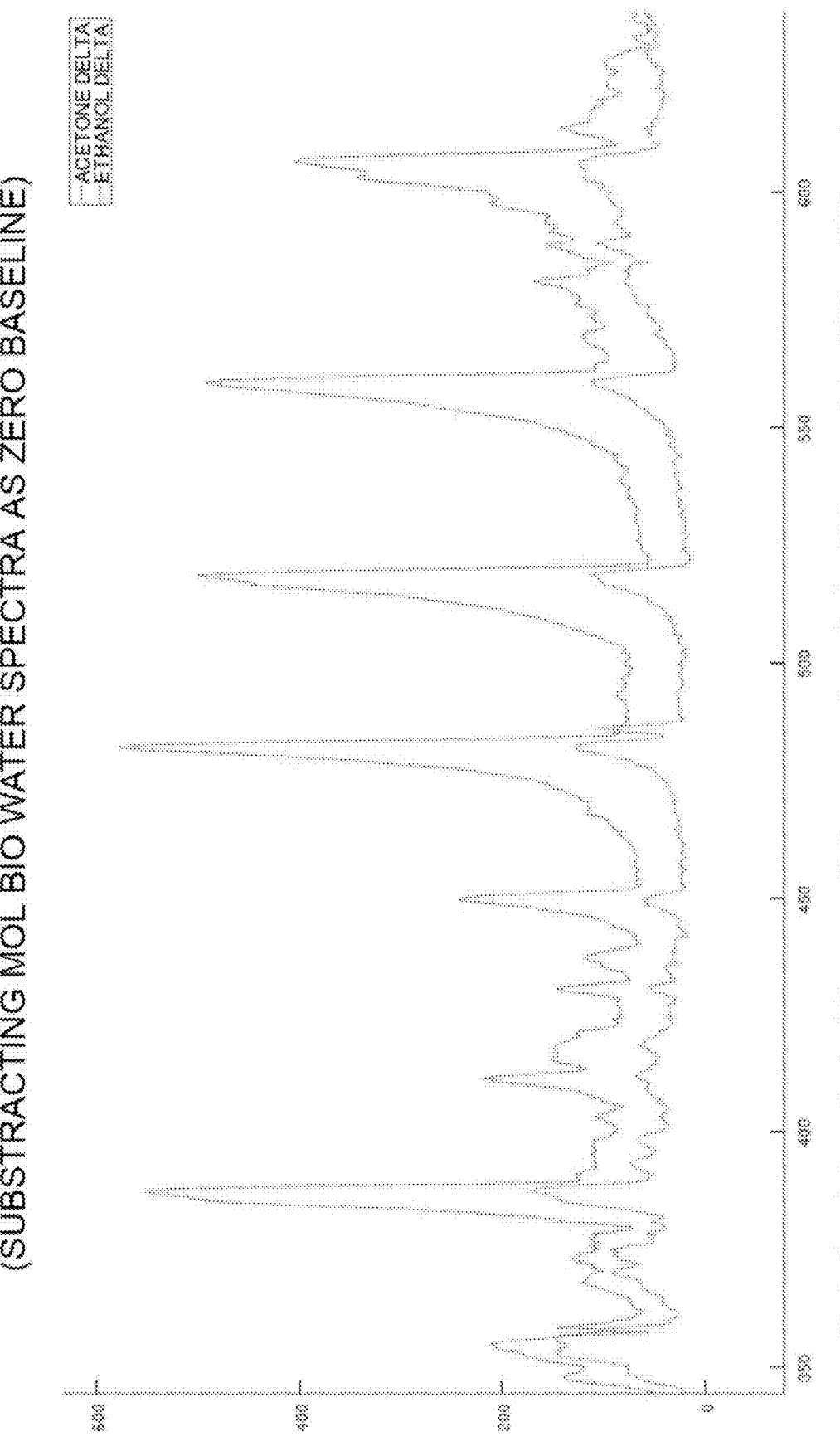
FIG. 12 illustrates a chart of intensity versus wavelength, comparing samples with acetone and ethanol, zoomed in between 350 and 650 nm with the water baseline subtracted, generated by the present invention.
Figure 13:
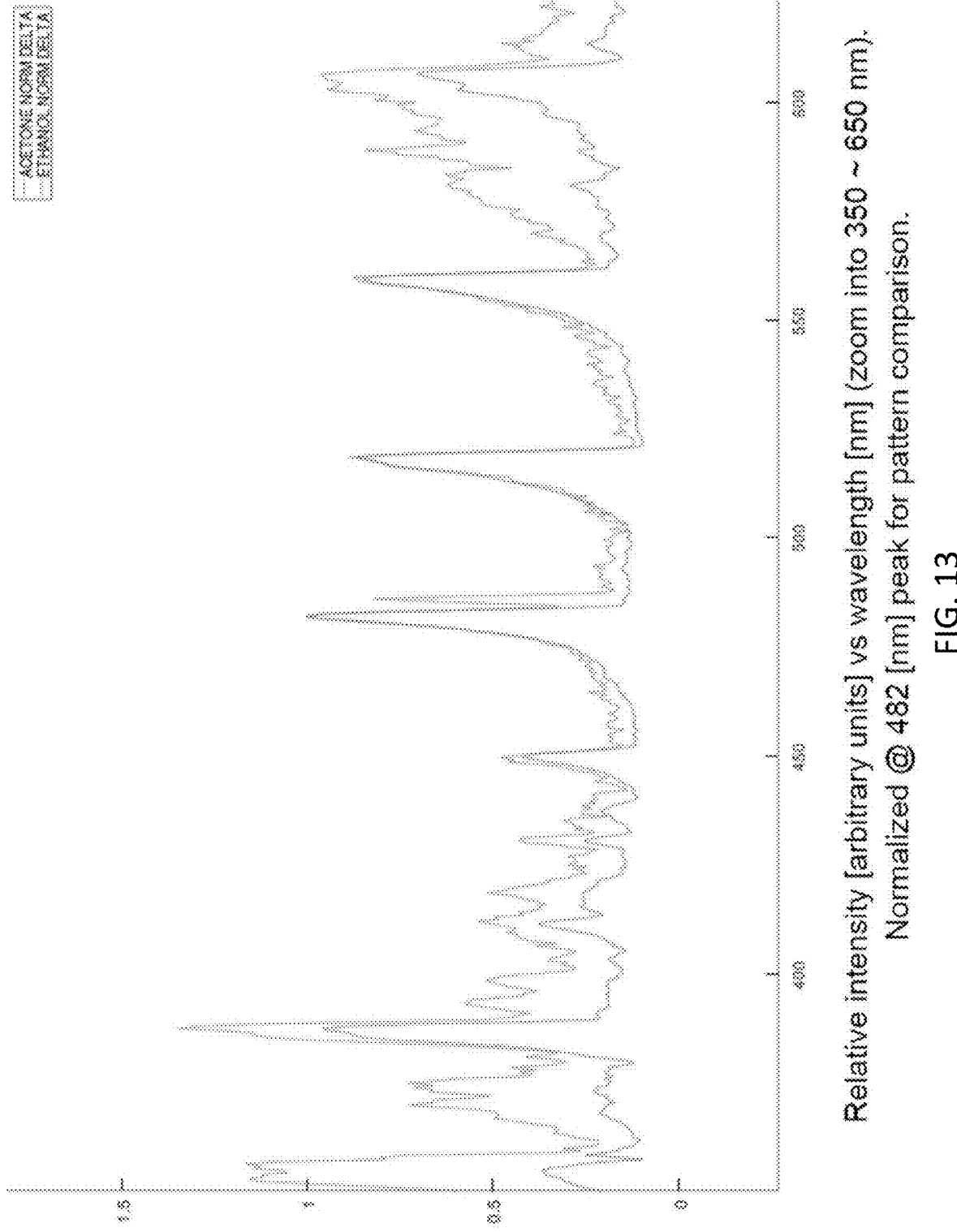
FIG. 13 illustrates a chart of intensity versus wavelength, comparing samples with acetone and ethanol, zoomed in between 350 and 650 nm normalized at a peak at 482 nm, generated by the present invention.
Figure 14:
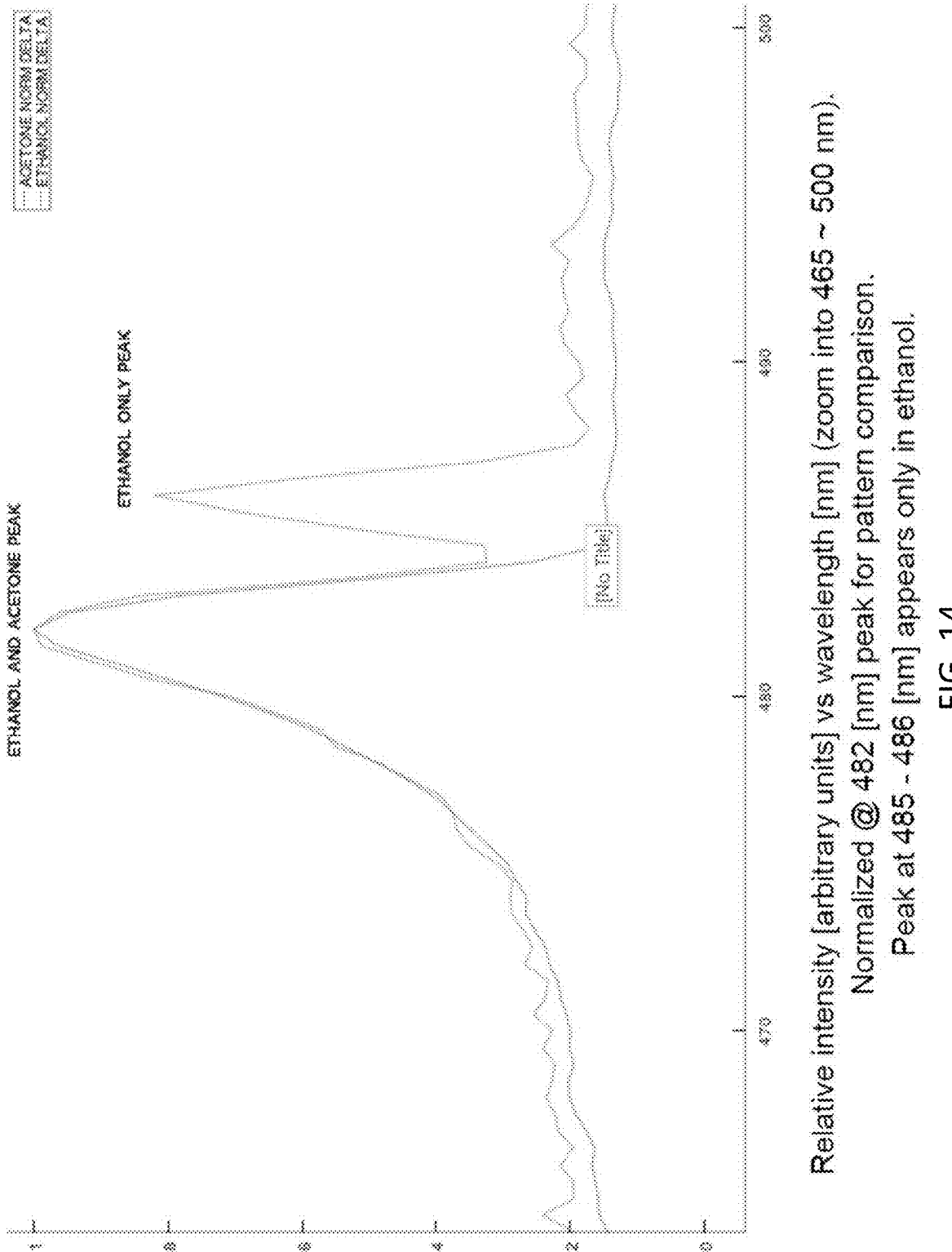
FIG. 14 illustrates a chart of intensity versus wavelength, comparing samples with acetone and ethanol, zoomed in between 465 and 500 nm, showing a peak unique to the ethanol signature at approximately 485 nm, generated by the present invention.

FIG. 10 illustrates a chart of intensity versus wavelength, comparing samples with acetone, ethanol, and MBG water generated by the present invention. FIG. 11 illustrates a chart of intensity versus wavelength, comparing samples with acetone, ethanol, and MBG water, zoomed in between 350 and 650 nm, generated by the present invention. FIG. 12 illustrates a chart of intensity versus wavelength, comparing samples with acetone and ethanol, zoomed in between 350 and 650 nm with the water baseline subtracted, generated by the present invention. FIG. 13 illustrates a chart of intensity versus wavelength, comparing samples with acetone and ethanol, zoomed in between 350 and 650 nm normalized at a peak at 482 nm, generated by the present invention. FIG. 14 illustrates a chart of intensity versus wavelength, comparing samples with acetone and ethanol, zoomed in between 465 and 500 nm, showing a peak unique to the ethanol signature at approximately 485 nm, generated by the present invention. FIGS. 10-14 demonstrate the present invention's ability to differentiate between different simple organic compounds, and particularly between different volatile organic compounds (VOCs).

Figure 15:
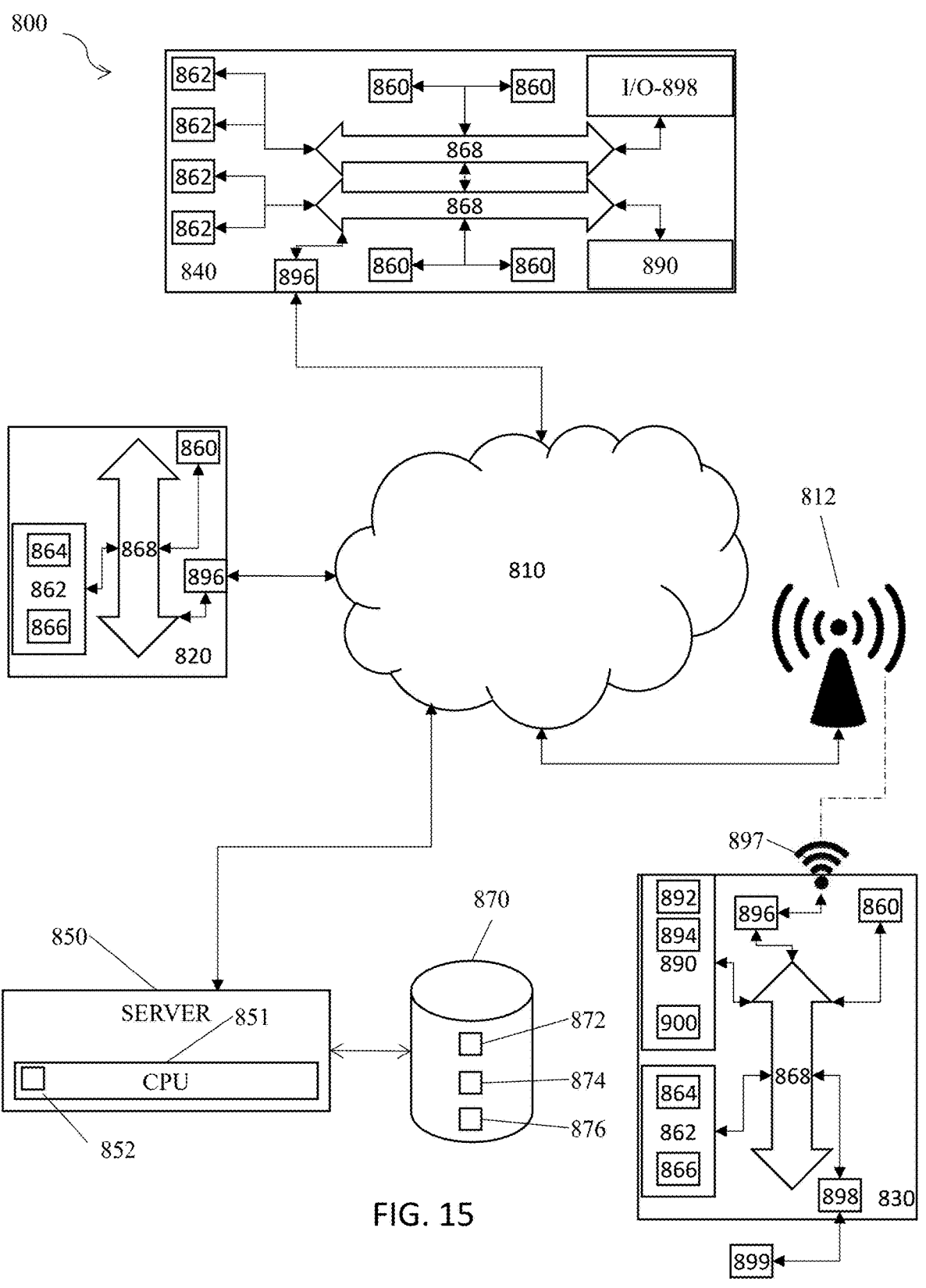
FIG. 15 is a schematic diagram of a system of the present invention.

FIG. 15 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 15, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 15, is operable to include other components that are not explicitly shown in FIG. 15, or is operable to utilize an architecture completely different than that shown in FIG. 15. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. An artificial intelligence (AI)-based system for automatically identifying molecules in a fluid sample, comprising:

one or more spectrometers or chemical analysis devices;

at least one reactor;

one or more servers configured to receive multi-dimensional training data from the one or more spectrometers or chemical analysis devices; and an AI module on the one or more servers;

wherein the one or more servers are configured to train the AI module using the multi-dimensional training data to automatically develop characteristic profiles for a plurality of known molecules or sets of molecules;

wherein the multi-dimensional training data corresponds with samples of the plurality of known molecules or sets of molecules;

wherein the at least one reactor is operable to ionize a fluid sample via a non-thermal plasma source;

wherein the one or more servers receive experimental data for the ionized fluid sample from a testing spectrometer;

wherein the AI module is operable to compare the experimental data to the multi-dimensional training data;

wherein the AI module is operable to analyze the experimental data, wherein the AI module automatically correlates spectrographic data from the experimental data with the characteristic profiles to identify molecules in the fluid sample; and wherein the AI module automatically generates a report based on comparison of the experimental data to the characteristic profiles for the plurality of molecules or sets of molecules.

2. The system of claim 1, wherein the one or more servers include cloud servers, and wherein the multi-dimensional training data received from the one or more spectrometers or chemical analysis devices is combined with public datasets and/or additional third party datasets.

3. The system of claim 1, wherein the multi-dimensional training data further includes synthetic data.

4. The system of claim 1, wherein the multi-dimensional training data includes data related to multiple different modalities of spectroscopic or other chemical analysis.

5. The system of claim 1, wherein the multi-dimensional training data includes data for at least one baseline of at least one sample.

6. The system of claim 1, wherein the AI module includes one or more machine learning (ML) models, deep learning (DL) models, neural networks (NNs), support vector machines (SVMs), and/or transformers.

7. The system of claim 1, wherein the one or more spectrometers includes one or more ultraviolet-visual (UV-VIS) spectrometers, one or more Raman spectrometers, one or more infrared (IR) spectrometers, one or more mass spectrometers, one or more nuclear magnetic resonance (NMR) spectrometers, one or more X-ray spectrometers, one or more optical emission spectrometers (OES), one or more atomic emission spectrometers (AES), and/or one or more Mossbauer spectrometers.

8. The system of claim 1, wherein the report includes indications of present identified molecules, indications of concentrations of the present identified molecules, and certainty values associated with each of the present identified molecules.

9. An artificial intelligence (AI)-based method for automatically identifying molecules in a fluid sample, comprising:

receiving multi-dimensional training data for one or more servers from one or more spectrometers or chemical analysis devices;

training an AI module using the multi-dimensional training data to automatically develop characteristic profiles for a plurality of known molecules or sets of molecules via the one or more servers;

ionizing a fluid sample via a non-thermal plasma source using at least one reactor;

receiving experimental data for the ionized fluid sample from a testing spectrometer via the one or more servers;

automatically analyzing the experimental data by automatically correlating spectrographic data from the experimental data with the characteristic profiles to identify biological molecules in the fluid sample using the AI module; and automatically generating a report with indications of present identified molecules based on comparison of the experimental data to the characteristic profiles for the plurality of molecules or sets of molecules using the AI module;

wherein the report includes indications of present identified molecules, indications of concentrations of the present identified molecules, and certainty values associated with each of the present identified molecules.

10. The method of claim 9, wherein the one or more servers include cloud servers, and further comprising combining the multi-dimensional training data received from the one or more spectrometers or chemical analysis devices with public datasets and/or additional third party datasets.

11. The method of claim 9, wherein the multi-dimensional training data includes data for at least one baseline of at least one sample.

12. The method of claim 9, wherein the multi-dimensional training data includes data related to multiple different modalities of spectroscopic or other chemical analysis.

13. The method of claim 9, wherein the multi-dimensional training data corresponds with samples of known molecules and/or compositions.

14. The method of claim 9, wherein the AI module includes one or more machine learning (ML) models, deep learning (DL) models, neural networks (NNs), support vector machines (SVMs), and/or transformers.

15. The method of claim 9, wherein the one or more spectrometers includes one or more ultraviolet-visual (UV-VIS) spectrometers, one or more Raman spectrometers, one or more infrared (IR) spectrometers, one or more mass spectrometers, one or more nuclear magnetic resonance (NMR) spectrometers, one or more X-ray spectrometers, one or more optical emission spectrometers (OES), one or more atomic emission spectrometers (AES), and/or one or more Mossbauer spectrometers.

16. The method of claim 9, wherein the multi-dimensional training data further includes synthetic data.

17. An artificial intelligence (AI)-based system for automatically identifying molecules in a fluid sample, comprising:

one or more spectrometers or chemical analysis devices;

at least one reactor;

one or more cloud servers configured to receive multi-dimensional training data from the one or more spectrometers or chemical analysis devices; and an AI module on the one or more cloud servers;

wherein the one or more cloud servers are configured to train the AI module using the multi-dimensional training data to automatically develop characteristic profiles for a plurality of known molecules or sets of molecules;

wherein the multi-dimensional training data received from the one or more spectrometers or chemical analysis devices is combined with public datasets and/or additional third party datasets;

wherein the at least one reactor is operable to ionize a fluid sample via a non-thermal plasma source;

wherein the one or more cloud servers receive experimental data for the ionized fluid sample from a testing spectrometer;

wherein the AI module is operable to compare the experimental data with the multi-dimensional training data;

wherein the AI module is operable to analyze the experimental data, and wherein the AI module automatically correlates spectrographic data from the experimental data with the characteristic profiles to identify molecules in the fluid sample; and wherein the AI module automatically generates a report based on comparison of the experimental data to the multi-dimensional training data for the plurality of molecules or sets of molecules.

18. The system of claim 17, wherein the multi-dimensional training data corresponds with samples of known molecules and/or compositions.

19. The system of claim 17, wherein the multi-dimensional training data includes data related to multiple different modalities of spectroscopic or other chemical analysis.

20. The system of claim 17, wherein the report includes indications of present identified molecules, indications of concentrations of the present identified molecules, and certainty values associated with each of the present identified molecules.

* * * * *